ns Patent [19]

Tesk et al.

[11] 4,010,048
[45] Mar. 1, 1977

[54] BONDING AGENT FOR FUSING PORCELAIN TO NONPRECIOUS METAL ALLOY

[75] Inventors: John A. Tesk, Woodridge; Henrietta M. Severa, Chicago; Ronald P. Dudek, River Grove; Peter Kosmos, Alsip, all of Ill.

[73] Assignee: Howmedica, Inc., New York, N.Y.

[22] Filed: Dec. 24, 1974

[21] Appl. No.: 536,327

[52] U.S. Cl. .................................. 148/24; 148/26
[51] Int. Cl.² ........................................ B23K 35/34
[58] Field of Search .................. 106/35, 45; 148/24, 148/26; 75/165

[56] References Cited

UNITED STATES PATENTS

| | | | |
|---|---|---|---|
| 2,914,435 | 11/1959 | Wasserman | 148/24 |
| 2,980,998 | 4/1961 | Coleman | 75/165 |
| 3,413,723 | 12/1968 | Wagner | 75/165 |
| 3,684,533 | 8/1972 | Conwicke | 148/24 |

*Primary Examiner*—Peter D. Rosenberg
*Attorney, Agent, or Firm*—Connolly & Hutz

[57] ABSTRACT

An extremely effective agent for achieving optimum bonding between a nonprecious dental alloy and porcelain is painted onto the alloy in slurry form and fired to prepare the surface of the alloy for bonding to porcelain. The bonding agent includes major proportions of fine gold powder, porcelain, liquid flux and a minor amount of fine zirconium oxide. The liquid flux is a low fusing flux dissolved in a liquid vehicle, such as glycerine or an alcohol. Suitable fluxes are boron oxide and its salts. The flux reacts to the porcelain and with the oxides which are formed on the alloy during firing to produce a low solubility, highly tenacious, adherent intermediate layer of oxides to which porcelain will readily and firmly adhere during subsequent application and firing.

15 Claims, No Drawings

BONDING AGENT FOR FUSING PORCELAIN TO NONPRECIOUS METAL ALLOY

CROSS REFERENCE TO RELATED APPLICATIONS

None.

BACKGROUND OF THE INVENTION

Dental restorations often require fusion of porcelain to a dental alloy which must be resistant to tarnish, oxidation and corrosion in a human oral environment or, in other words, is biocompatible. Nonprecious alloys which are highly effective for dental use are described in copending commonly assigned application for U.S. Pat. Ser. No. 536,328 Filed Dec. 24, 1974 [PC (HOW) 5594]. An agent is required to achieve optimum bonding between the porcelain and the alloy. This agent must react with the porcelain and alloy during firing to produce a low solubility, highly tenacious, adherent intermediate layer of oxides on the metal to which the porcelain will tightly adhere after subsequent application and firing. An object of this invention is to provide an effective bonding agent of this type, and another object is to provide such an economical bonding agent of readily available materials.

SUMMARY

In accordance with this invention an extremely effective bonding agent for achieving optimum bonding between a nonprecious dental alloy and porcelain is obtained from the following formulations which are painted onto the alloy in slurry form and fired to prepare the surface for bonding to procelain.

| Constituent | Proportional Range | Preferred Composition |
| --- | --- | --- |
| Gold Powder (1.5 microns) | 34.0–52.0 | 34.96 |
| Hi-Life Body Porcelain | 13.1–30.6 | 26.22 |
| Zirconium Oxide (10 microns) | 4.4–8.74 | 8.74 |
| Liquid Flux | Balance | 30.08 |

The liquid flux is a low fusing "flux" soluble in a vehicle such as glycerine or an alcohol. The essential characteristic is that the flux will react with the porcelain and with oxides which are formed on the alloy during firing of the bonding agent, to produce a low solubility, highly tenacious, adherent intermediate layer of oxides to which porcelain will adhere during subsequent application and firing. The addition of a thixotropic agent such as Cab-o-Sil, maintains all powders in solution for more consistent application and improved "painting" characteristics.

DESCRIPTION OF THE PREFERRED EMBODIMENTS

Particular examples of alloys to which this invention is applicable are listed below in Examples I-V giving preferred compositions and proportional ranges in percentages by weight. These alloys have been found particularly useful for dental service and are particularly effective for fusion and tight adherence to porcelain.

EXAMPLE I

| Element | Proportional Range | Preferred Composition |
| --- | --- | --- |
| Nickel | Balance | 75.4 |
| Chromium | 10.0–15.0 | 13.5 |
| Molybdenum | 1.0–7.0 | 5.0 |
| Aluminum | 1.0–5.0 | 3.0 |
| Silicon | 0.5–2.0 | 1.0 |
| Manganese | 1.01–0.2 | 0.1 |
| Iron | 0–5.0 | 1.5 |
| Strontium, Lanthanum and/or Zirconium individually or as a combination of Strontium and Zirconium | 0.2–2.0 | 0.5 |
| | | 100.0% |

EXAMPLE II

| Element | Proportional Range | Preferred Composition |
| --- | --- | --- |
| Nickel | Balance | 78.4 |
| Chromium | 10.0–15.0 | 13.5 |
| Molybdenum | 1.0–5.0 | 1.5 |
| Aluminum | 1.0–5.0 | 3.0 |
| Silicon | 0.5–2.0 | 1.0 |
| Manganese | 0.01–0.2 | 0.1 |
| Strontium, Lanthanum and/or Zirconium individually or as a combination of Strontium and Zirconium | 0.2–2.0 | 0.5 |
| Tungsten | 0.5–5.0 | 2.0 |
| | | 100.0% |

EXAMPLE III

| Element | Proportional Range | Preferred Composition |
| --- | --- | --- |
| Nickel | Balance | 78.1 |
| Chromium | 10.0–22.0 | 13.5 |
| Molybdenum | 0.0–3.0 | 1.5 |
| Aluminum | 1.0–5.0 | 3.0 |
| Silicon | 0.5–2.0 | 1.0 |
| Manganese | 0.01–0.2 | 0.1 |
| Strontium, Lanthanum and/or Zirconium individually or as a combination of Strontium and Zirconium | 0.0–2.0 | 0.5 |
| Gallium | 1.0–3.0 | 2.0 |
| Iron | 0.0–1.0 | 0.3 |
| | | 100.0% |

EXAMPLE IV

| Element | Proportional Range | Preferred Composition |
| --- | --- | --- |
| Nickel | Balance | 75.4 |
| Chromium | 10.0–15.0 | 13.5 |
| Molybdenum | 1.0–7.0 | 5.0 |
| Aluminum | 1.0–5.0 | 3.0 |
| Silicon | 0.5–2.0 | 1.0 |
| Manganese | 1.01–0.2 | 0.1 |
| Tungsten | 0–5.0 | 1.5 |
| Strontium, Lanthanum and/or Zirconium individually or as a combination of Strontium and Zirconium | 0.2–2.0 | 0.5 |
| | | 100.0% |

EXAMPLE V

| Element | Proportional Range | Preferred Composition |
| --- | --- | --- |
| Nickel | Balance | 75.4 |
| Chromium | 10.0–15.0 | 13.5 |
| Molybdenum | 1.0–7.0 | 5.0 |

EXAMPLE V-continued

| Element | Proportional Range | Preferred Composition |
|---|---|---|
| Aluminum | 1.0–5.0 | 3.0 |
| Silicon | 0.5–2.0 | 1.0 |
| Manganese | 1.01–0.2 | 0.1 |
| Iron | 0–2.5 | 1.0 |
| Strontium, Lanthanum and/or Zirconium individually or as a combination of Strontium and Zirconium | 0.2–2.0 | 0.5 |
| Tungsten | 0–2.5 | 0.5 |
|  |  | 100.0% |

All combinations of strontium, lanthanum and zirconium within the recited ranges are effective and a useful such constituent is a 50%—50% combination of strontium and zirconium.

The bonding system that is necessary to achieve optimum bonding between such alloy and porcelain is as follows in percent by weight:

| Constituent | Proportional Range | Preferred Composition |
|---|---|---|
| Gold Powder (5–15 microns) | 34.0–52.0 | 34.96 |
| Porcelain | 13.1–30.6 | 26.22 |
| Zirconium Oxide (10 microns) | 4.4–8.74 | 8.74 |
| Liquid Flux | Balance | 30.08 |

The porcelain is for example, "Hi-Life" Body Porcelain, "Hi-Life" is a trademark of Howmedica Inc., Dental Division, Chicago, Illinois for a porcelain having approximately the following formulation in percentages by weight.

| Constituent | Composition |
|---|---|
| $SiO_2$ | 68.64 |
| $Al_2O_3$ | 13.76 |
| CaO | 0.36 |
| $K_2O$ | 13.46 |
| $Na_2O$ | 2.29 |
| $Li_2O$ | 1.49 |

The porcelain can also be any porcelain which has a similar formulation, is intended for fabrication of fused porcelain prosthesis, and has a softening point of about 1200°–1400° F.

The liquid flux or bonding agent liquid is a low fusing "flux" soluble in a vehicle such as glycerine or an alcohol. The flux may be boron oxide or its salts, such as sodium borate or light element oxides, i.e. $Li_2O$, $Na_2O$ and those light element oxides of the first column of the periodic table. The essential characteristic is that the flux will react with the porcelain and with oxides which are formed on the alloy during firing of the bonding agent, to produce a low solubility, highly tenacious, adherent intermediate layer of oxides to which porcelain will adhere during subsequent application and firing. A range of compositions is effective under these conditions, and a typical composition within such range is as follows:

500 cc. glycerine
10–30 grams boric anhydride
1.14 cc. wetting agent

The proportional range involves such composition is as follows:

| Constituent | Proportional Range | | |
|---|---|---|---|
| Glycerine | 300 | to | 600 cc. |
| Boric Anhydride | 10 | to | 30 grams |
| Wetting Agent | 0.5 | to | 2.0 cc. |

Another highly suitable bonding agent utilizing the addition of a thixotropic agent such as Cab-o-Sil, maintains all powders in solution for more consistent application and improve the "painting" characteristics. Such a formulation is as follows by weight percent

| Constituent | Proportional Range | Preferred Example |
|---|---|---|
| Glycerine | Balance | 94.954 |
| $B_2O_3$ | 1.50 to 4.52 | 2.502 |
| Victawet No. 12 | .085 to .338 | 0.237 |
| Cab-o-Sil | 1.54 to 3.07 | 2.307 |

Victawet No. 12 is the trademark of Victor Chemical Works for a non-foaming non-ionic wetting agent of the type $(RO)PO(OR')_2$, where R is a medium-chain alkyl group, and R' is a water-solubilizing group. $P_2O_5$ content is 16%. It is an amber-colored liquid; sp.gr. 1.121; pH, 4.7 (0.5% solution); surface tension, 28.8 dynes/cm. (0.2% solution 29° C); Draves test, 9.2 sec. at 0.6% conc., and 32 sec. at 0.2% conc. (in hard water) insoluble in naphtha; soluble in alcohols, acetone toluene; forms a milky solution in water. Uses: As a wetting agent in acid and alkaline solutions; and as a carrier for acid dyes. It provides level shades and uniform penetration in package dying of nylon, etc.

Cab-o-sil is the trademark of Godfrey L. Cabot, Inc. for a colloidal silica prepared in a hot gaseous environment by a vapor-phase hydrolysis of a silicon compound instead of by the usual aqueous precipitation process. Its outstanding properties are high chemical purity, low water content, enormous external surface area, and high degree of particle separation. Cab-o-sil functions in extremely small quantities as a reinforcing agent in rubber and plastics, a suspending and flatting agent in paints, as a thixotropic agent in various resins, as an emulsion stabilizer, and as a thickening and gelling agent.

The purpose of the bonding agent is to achieve a tenacious bond between the metal and porcelain so as to prevent any potential chipping or breaking away of the porcelain from the metal while the dental appliance is in use in the mouth. The bond is achieved by the interaction between the bonding agent and the particular oxides that are formed on the alloy during the firings that take place in the processing of the porcelain.

The manner in which the aforementioned liquid flux is used as a bonding agent is as follows: A thin slurry is made using the Liquid Flux and the opaque or undercoat porcelain. This is then painted onto the appliance in the areas which are to receive porcelain and the slurry is then fired. A specific ratio of powder/liquid is not required. The conditions which are necessary for success are that the slurry is paintable and, after painting, produces a general blocking out of the underlying metal color.

Another manner of describing the liquid flux is stated as follows in the indicated percentages by weight

| Constituent | Proportional Range | Preferred Example |
|---|---|---|
| Reactive oxide agent | 1.54 to 4.63 | 2.56 |
| Compatible liquid vehicle | Balance | 97.20 |
| Wetting Agent | .086 to .35 | 0.24 |

The constituents are the same as those otherwise stated herein and can also include a thixotropic agent.

We claim:

1. A bonding agent for fusing a metal alloy with porcelain consisting essentially of the following constituents in percentages by weight:

| Constituent | Proportional Range |
|---|---|
| Gold Powder (15 microns) | 34.0–52.0 |
| Porcelain | 13.1–30.6 |
| Zirconium Oxid (10 microns) | 4.4–8.74 |
| Liquid Flux(capable of reaction to form layers of tenacious oxides on alloy to which porcelain adheres) | Balance |

2. A bonding agent as set forth in claim 1 wherein the liquid flux comprises an oxide flux solution capable of reacting with the porcelain and oxides which form on the alloy during firing to form an adherent layer of oxides to which the porcelain will adhere.

3. A bonding agent as set forth in claim 2 wherein the liquid flux includes glycerine as a liquid vehicle.

4. A bonding agent as set forth in claim 2 wherein the flux includes an alcohol as a liquid vehicle.

5. A bonding agent as set forth in claim 2 wherein the liquid flux includes an oxide constituent comprising boric anhydride.

6. A bonding agent as set forth in claim 2 wherein the liquid flux includes an oxide constituent comprising boron oxide.

7. A bonding agent as set forth in claim 2 wherein the liquid flux includes an oxide constituent comprising sodium borate.

8. A bonding agent as set forth in claim 2 wherein the liquid flux includes an oxide constituent comprising light element oxide.

9. A bonding agent as set forth in claim 2 wherein the liquid flux includes an oxide constituent comprising an oxide selected from the group consisting of lithium oxide, sodium oxide and light element oxides of the first column of the periodic table.

10. A bonding agent as set forth in claim 1 wherein the liquid flux includes a wetting agent.

11. A bonding agent as set forth in claim 1 wherein the liquid flux comprises the following ranges of constituents in the indicated percentages by weight;

| Constituent | Proportional Range |
|---|---|
| Glycerine | Balance |
| $B_2O_3$ | 1.50 to 4.52 |
| Victawet No. 12 | .085 to .338 |
| Cab-o-sil | 1.54 to 3.07 |

12. A bonding agent as set forth in claim 11 wherein the liquid flux comprises the following constituents in the indicated ranges of percentages by weight:

| Constituent | Percentages by weight |
|---|---|
| Reactive oxide agent | 1.54 to 4.63 |
| Compatible liquid vehicle | Balance |
| Wetting Agent | .086 to .35 |

13. A bonding agent as set forth in claim 12 wherein a minor amount of a thixotropic agent is added to the liquid flux.

14. A bonding agent as set forth in claim 12 wherein the reactive oxide agent is selected from the group consisting of boric anhydride, boron oxide, lithium oxide, sodium oxide and light element oxides of the first column of the periodic table.

15. A bonding agent as set forth in claim 13 wherein the compatible liquid vehicle is a liquid selected from the group consisting of glycerine and alcohol.

* * * * *